(12) United States Patent
Whitten et al.

(10) Patent No.: US 8,598,053 B2
(45) Date of Patent: Dec. 3, 2013

(54) MATERIALS INCORPORATING ANTIMICROBIAL POLYMERS

(75) Inventors: David G. Whitten, Albuquerque, NM (US); Linnea K. Ista, Albuquerque, NM (US); Thomas S. Corbitt, Albuquerque, NM (US); Motokatsu Ogawa, Gainesville, FL (US); Kirk S. Schanze, Gainesville, FL (US); Gabriel P. Lopez, Durham, NC (US); Ramanathan Nagarajan, Natick, MA (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/503,067

(22) PCT Filed: Oct. 12, 2010

(86) PCT No.: PCT/US2010/052332
§ 371 (c)(1),
(2), (4) Date: Jul. 13, 2012

(87) PCT Pub. No.: WO2011/044580
PCT Pub. Date: Apr. 14, 2011

(65) Prior Publication Data
US 2012/0271023 A1   Oct. 25, 2012

Related U.S. Application Data

(60) Provisional application No. 61/250,099, filed on Oct. 9, 2009, provisional application No. 61/345,646, filed on May 18, 2010.

(51) Int. Cl.
*B32B 5/02* (2006.01)

(52) U.S. Cl.
USPC ............................. 442/123; 442/59; 527/313

(58) Field of Classification Search
USPC ..................... 527/313; 442/123, 59
See application file for complete search history.

(56) References Cited

U.S. PATENT DOCUMENTS

2003/0168756 A1* 9/2003 Balkus et al. ................. 264/10
2005/0148254 A1* 7/2005 Lu et al. ...................... 442/123

FOREIGN PATENT DOCUMENTS

WO   WO-2009158606 A2   12/2009
WO   WO-2011044580 A3   4/2011

OTHER PUBLICATIONS

International Application Serial No. PCT/US2010/052332, International Preliminary Report on Patentability mailed Apr. 11, 2012, 7 pgs.
International Application Serial No. PCT/US2010/052332, International Search Report mailed Jun. 24, 2011, 4 pgs.
International Application Serial No. PCT/US2010/052332, Written Opinion mailed Jun. 24, 2011, 6 pgs.

* cited by examiner

*Primary Examiner* — James J Seidleck
*Assistant Examiner* — Peter A Salamon
(74) *Attorney, Agent, or Firm* — Schwegman Lundberg & Woessner, P.A.

(57) ABSTRACT

The present disclosure describes the manufacture and use of soft surfaces such as fabrics bearing surface-grafted antimicrobial polymers.

17 Claims, 4 Drawing Sheets

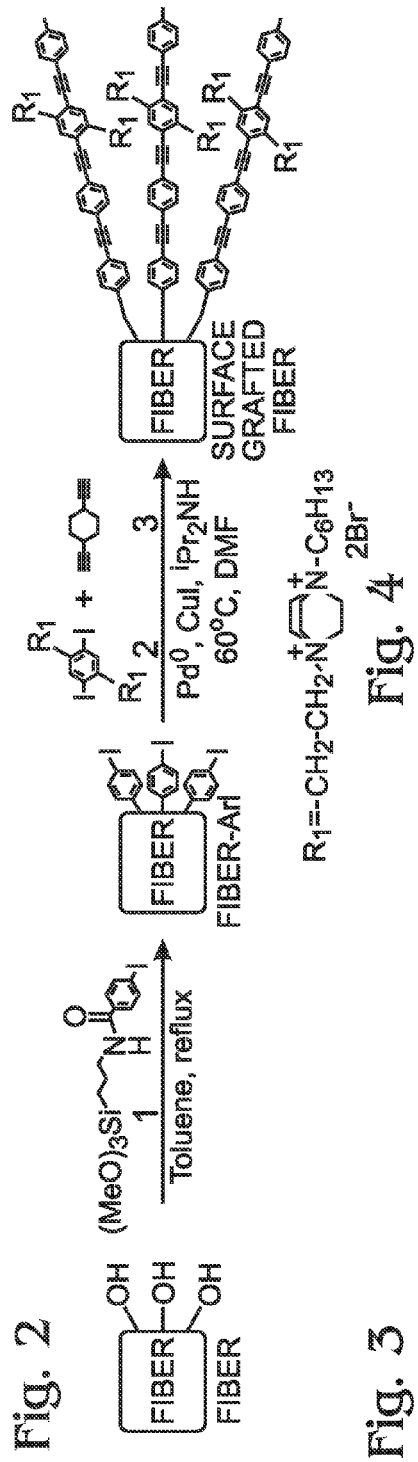
Fig. 2
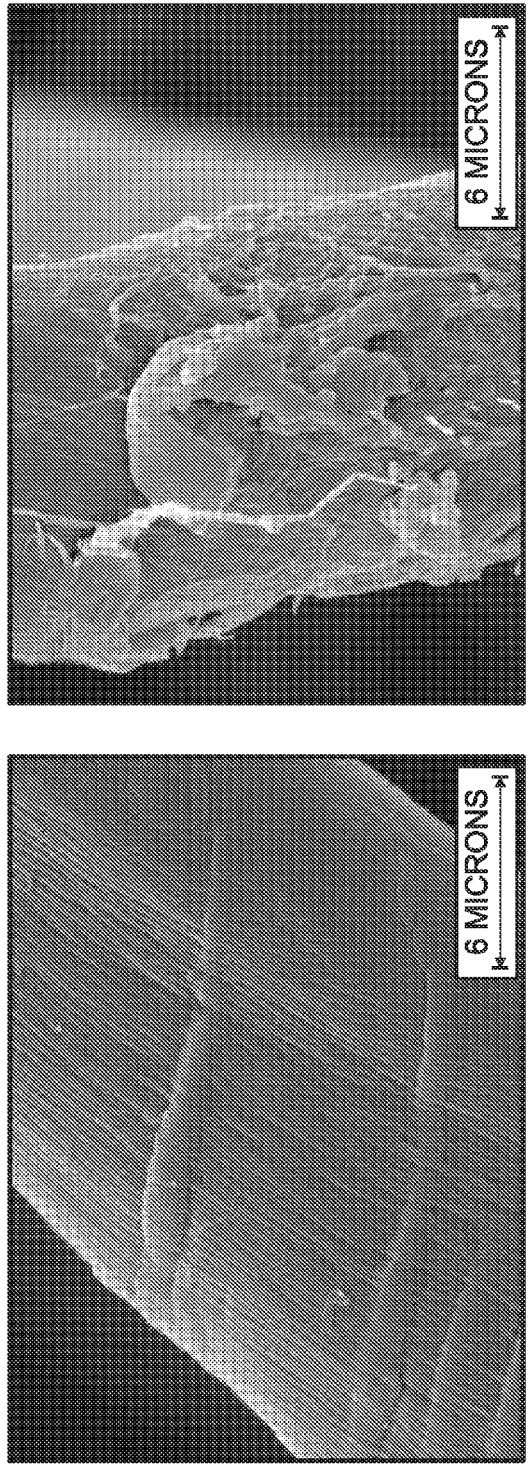
Fig. 3
Fig. 4

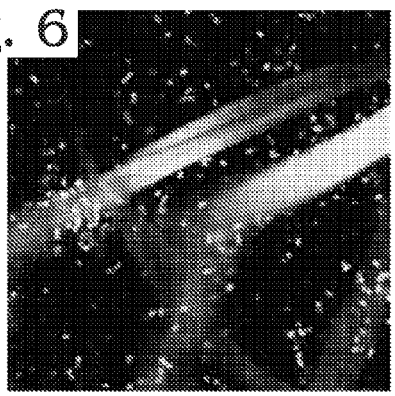
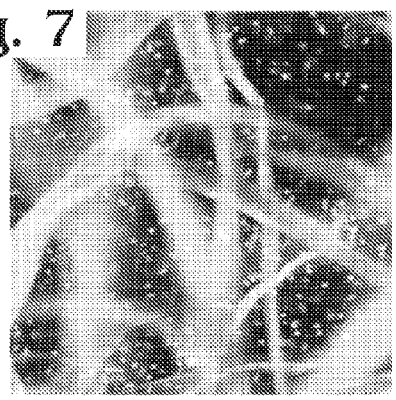
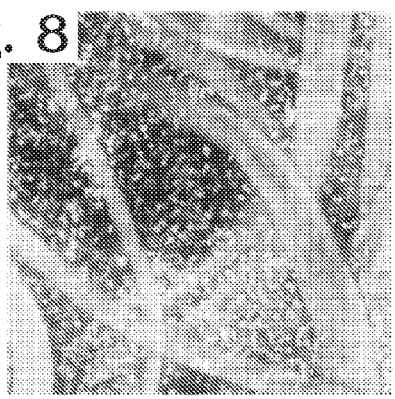
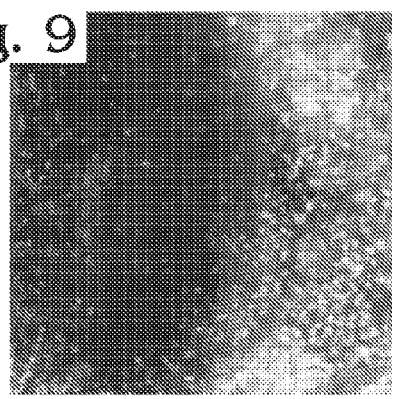
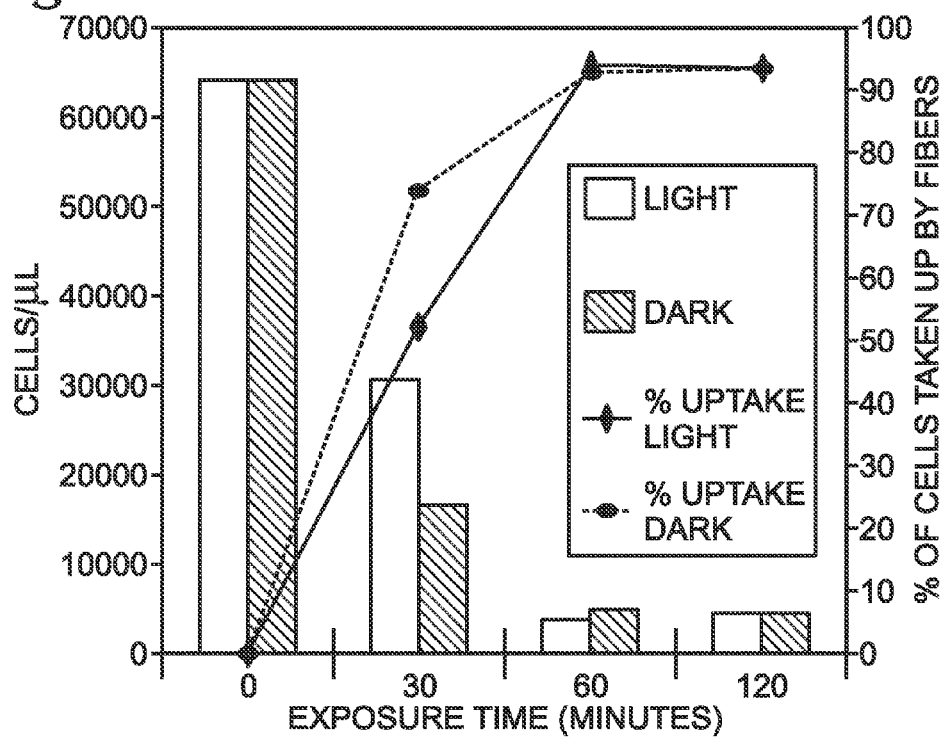

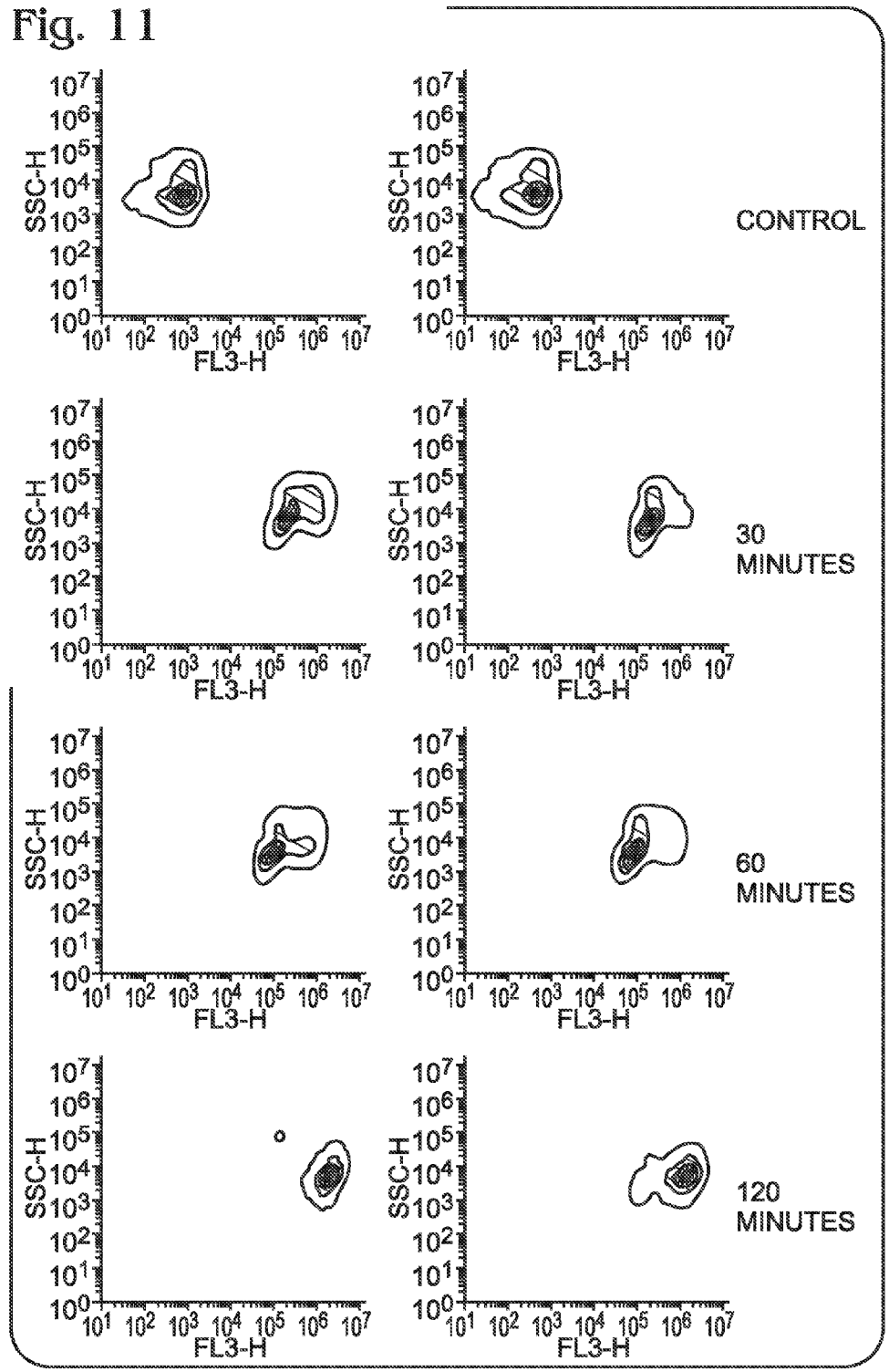

MATERIALS INCORPORATING ANTIMICROBIAL POLYMERS

CROSS-REFERENCE TO RELATED APPLICATIONS

The following application claims benefit of U.S. Provisional Application Nos. 61/250,099 filed Oct. 9, 2009 and 61/345,646, filed May 18, 2010, both of which are hereby incorporated by reference in their entirety.

STATEMENT REGARDING GOVERNMENT SPONSORED RESEARCH

This invention was made with Government support under Grant No. AB07CBT006 awarded by the Defense Threat Reduction Agency. The U.S. Government has certain rights in this invention.

BACKGROUND

Until the 20$^{th}$ century, up to 73% of human mortality could be attributed to infections. (See, e.g., Crimmins, E. M., and C. E. Finch. 2006. Infection, inflammation, height, and longevity. Proceedings of the National Academy of Sciences of the United States of America 103:498-503.) Recognition of the germ theory of disease led to increased sanitation and the development of antimicrobial therapies, which reduced this limitation on human longevity. While the chances that one will die from an infection or infectious disease is small compared to previous centuries, within the hospital setting, the chances of acquiring a possibly fatal infection continues to rise. (See e.g, Scott, R. D. 2009. The direct medical costs of healthcare associated infections in US hospitals and the benefits of prevention. Centers for Disease Control and Prevention.) The extensive use of antibiotics, although revolutionary and effective, has nonetheless resulted in acquisition of resistance genes by hospital strains of organisms, making nosocomial infections increasingly hard to treat. A recent estimate states that 1.7 million such infections occur annually with a death toll of 100,000 people per year and a direct cost of $45 billion dollars.

Bacteria attached to solid surfaces can form a major reservoir for pathogenic organisms. In addition, attached cells can rapidly form biofilms, which are not only more resistant to disinfection than single or planktonic bacteria, but also demonstrate increased genetic exchange. Accompanied by selective pressure from the myriad of antibiotics and disinfectants used within the hospital setting, lateral genetic exchange, which occurs even between genera, can result in the formation of multiply resistant organisms. According to the recent reports, multiply resistant bacteria are responsible for 16% of hospital acquired infections. (See e.g., Hidron, A. I., J. R. Edwards, and J. Patel. 2009. Antimicrobial-resistant pathogens associated with healthcare-associated infections: annual summary of data reported to the National Healthcare Safety Network at the Centers for Disease Control and Prevention, 2006-2007 (vol 29, pg 996, 2008). Infection Control and Hospital Epidemiology 30:-. and Seigal, J., E. Rhinehart, M. Jackson, and L. Chiarello. 2006. Management of multi-drug resistant organisms in healthcare settings, 2006. Centers for Disease Control and Prevention.)

Infection control has, thus, become a major focus of modern hospital infection management. Isolation of infected patients, the use of gowns and gloves by healthcare personnel, frequent handwashing and assiduous cleaning of hard surfaces have all been shown to be effective in controlling even the most resistant pathogens. Only recently have hospital textiles been considered an important reservoir for pathogens; a recent mathematical model predicts that organisms attached to textiles can contaminate both health care workers' hands and room air. (See, e.g, Nicas, M., and G. Sun. 2006. An integrated model of infection risk in a health-care environment. Risk Analysis 26:1085-1096.) This model has been verified in a meta-analysis on the transfer of multiply resistant organism colonization patient beds demonstrated that not only bedlinens, but pillows, mattresses and even fire blankets under mattresses may be a reservoir for infection, with transfer of the organisms to the air and hands occurring during bedmaking. (See e.g., Creamer, E., and H. Humphreys. 2008. The contribution of beds to healthcare-associated infection: the importance of adequate decontamination. Journal of Hospital Infection 69:8-23.) One effective strategy for preventing the airborne spread of infection is the judicious use of curtains, (Ching, W. H., M. K. H. Leung, D. Y. C. Leung, Y. Li, and P. L. Yuen. 2008. Reducing risk of airborne transmitted infection in hospitals by use of hospital curtains. Indoor and Built Environment 17:252-259.) but, these, too, may serve as a reservoir for pathogens, including drug resistant strains. (Klakus, J., N. L. Vaughan, and T. C. Boswell. 2008. Meticillin-resistant *Staphylococcus aureus* contamination of hospital curtains. Journal of Hospital Infection 68:189-190. and Trillis, F., E. C. Eckstein, R. Budavich, M. J. Pultz, and C. J. Donskey. 2008. Contamination of Hospital Curtains With Healthcare-Associated Pathogens. Infection Control and Hospital Epidemiology 29:1074-1076.) Such concerns are not limited to the hospital setting; household shower curtain biofilms can be a major reservoir for opportunistic pathogens. (Kelley, S. T., U. Theisen, L. T. Angenent, A. S. Amand, and N. R. Pace. 2004. Molecular analysis of shower curtain biofilm microbes. Applied and Environmental Microbiology 70:4187-4192.) Release of attached pathogens is thus, undesirable, and a truly effective biocidal fabric would both retain and kill attached organisms.

A recent review (Gao, Y., and R. Cranston. 2008. Recent advances in antimicrobial treatment of textiles. Textile Research Journal 78:68-72) has explored different antimicrobial textiles. These include not only those used in healthcare settings, but also those used to enhance personal hygiene and prevent deterioration of fabric. Among the most effective strategies are those using heavy metals and their salts, quaternary ammonium, polyhexamethylene biguanides, trichlosan, N-halamine compounds, and peroxyacids. While all are effective, all have substantial drawbacks, including the need for regeneration (N-halamines, peroxyacids), low biocidal activity (trichlosan, PHMB), toxic by products (trichlosan) and development of resistant strains Accordingly, there is a substantial need for new methods for providing antimicrobial protection to textiles and novel textiles having antimicrobial properties.

BRIEF DESCRIPTION OF THE DRAWINGS

FIG. 2 is a diagram showing a method of attaching a conjugated polyelectrolyte to fiber according to an embodiment of the present disclosure.

FIG. 3 shows a scanning electron micrograph of individual untreated cotton fibers FIG. 4 shows a scanning electron micrograph of individual DABCO-coated cotton fibers.

FIG. 6 is a confocal laser scanning image showing the uptake and killing of B. atrophaeus vegetative cells on DABCO-cotton fibers.

FIG. 7 is a confocal laser scanning image showing the uptake and killing of B. atrophaeus vegetative cells on DABCO-cotton fibers.

FIG. 8 is a confocal laser scanning image showing the uptake and killing of B. atrophaeus vegetative cells on DABCO-cotton fibers.

FIG. 9 is a confocal laser scanning image showing the uptake and killing of B. atrophaeus vegetative cells on DABCO-cotton fibers.

FIG. 10 demonstrates the number of cells present in the suspending fluid over time using flow cytometry.

FIG. 11 provides flow cytometry results of suspensions of B. atrophaeus after exposure to DABCO-cotton fibers in the dark (left column) and the light (right column).

SUMMARY

According to an embodiment the present disclosure provides the manufacture and use of fibers, fabrics, and other soft surfaces bearing surface-grafted antimicrobial polymers.

DETAILED DESCRIPTION

Previous studies have shown that certain conjugated polyelectrolytes such as Poly(phynylene ethyneylene) (PPE)-based cationic conjugated polyelectrolytes (CPEs) and cationic phynylene ethynylene oligomers (OPEs) exhibit dark and light-activated biocidal activity against Gram positive and Gram negative bacteria and bacterial spores. More recent work has shown that coatings on solid surfaces (both physisorbed, chemisorbed, or covalently grown) are also effective at entrapping bacteria and killing them either in the dark or upon irradiation with light absorbed by the conjugated polyelectrolyte. (See, e.g., Yanli Tang, Zhijun Zhou, Katsu Ogawa, Gabriel P. Lopez, Kirk S. Schanze, David G. Whitten, "Synthesis, Self-Assembly and Photophysical Behavior of Oligo Phenylene Ethynylenes: From Molecular to Supramolecular Properties", *Langmuir,* 2009, 25, 21-25. Yanli Tang, Zhijun Zhou, Katsu Ogawa, Gabriel P. Lopez, Kirk S. Schanze, David G. Whitten, "Photophysics and Self-Assembly of Symmetrical and Unsymmetrical Cationic Oligophenylene Ethynylenes", *J. Photochem. Photobiol.* A, 2009, in press. Ogawa, K.; Chemburu, S.; Lopez, G. P.; Whitten, D. G.; Schanze, K. S. "Conjugated Polyelectrolyte-Grafted Silica Micro spheres" *Langmuir,* 2007, 23, 4541-4548.)

Figure 1:
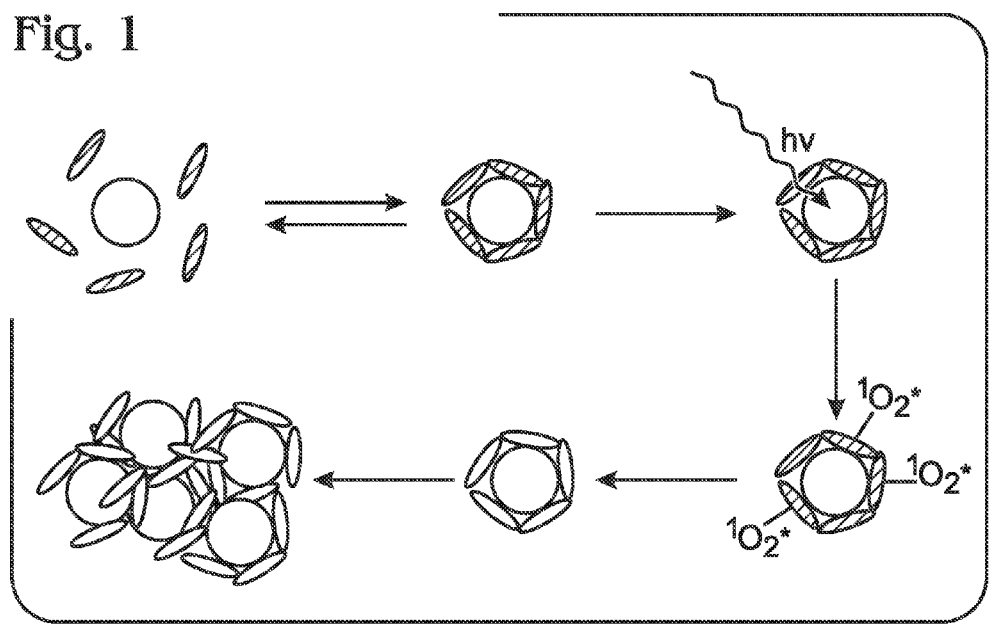
FIG. 1 is a diagram showing the mechanism of biocidal action for conjugated polyeletrolytes (CPEs).

As shown in FIG. 1, the CPE showing light-activated biocidal activity against both Gram positive and Gram negative bacteria have been found to first reversibly, and then subsequently irreversibly, attach bacteria to the surfaces on which they are coated by adsorption or covalently surface grafted (step i). (See, e.g., Sireesha Chemburu, Thomas Corbitt, Linnea Ista, Eunkyung Ji, Julia Fulghum, Gabriel Lopez, Katsu Ogawa, Kirk Schanze, David Whitten, "Light-Induced Biocidal Action of Conjugated Polyelectrolytes Supported on Colloids" *Langmuir,* 2008, 24, 11053-11062; Thomas S. Corbitt, Jonathan R. Sommer, Sireesha Chemburu, Katsu Ogawa, Linnea K. Ista, Gabriel P. Lopez, David G. Whitten, Kirk S. Schanze, "Conjugated Polyelectrolyte Capsules: Light-Activated Antimicrobial Micro "Roach Motels" *ACS Appl. Mater. Interfaces,* 2009 1, 48-52; and Thomas S. Corbitt, Liping Ding, Eunkyung Ji, Linnea K. Ista, Katsu Ogawa, Gabriel P. Lopez, Kirk S. Schanze, David G. Whitten, "Light and Dark Biocidal Activity of Cationic Poly(arylene ethynylene) Conjugated Polyelectrolytes" *Photochemical and Photobiological Sciences,* 2009, 8:998-1005 each of which is hereby incorporated by reference.)

The light-activated process is initiated when the CPE are photoexcited with visible light and then form triplet states that can generate singlet oxygen at the CPE-bacteria interface. The singlet oxygen can either kill the bacteria directly or, in turn, generate other corrosive reactive oxygen species (steps iii and iv). See, e.g., Sireesha Chemburu, Thomas Corbitt, Linnea Ista, Eunkyung Ji, Julia Fulghum, Gabriel Lopez, Katsu Ogawa, Kirk Schanze, David Whitten, "Light-Induced Biocidal Action of Conjugated Polyelectrolytes Supported on Colloids" *Langmuir,* 2008, 24, 11053-11062, incorporated by reference, above.

While we have shown this mechanism applies specifically for CPE coatings, we believe it should generally apply to other formats, including the hollow microcapsules we have found to have remarkable abilities to capture and subsequently kill bacteria. See, e.g., Thomas S. Corbitt, Jonathan R. Sommer, Sireesha Chemburu, Katsu Ogawa, Linnea K. Ista, Gabriel P. Lopez, David G. Whitten, Kirk S. Schanze, "Conjugated Polyelectrolyte Capsules: Light-Activated Antimicrobial Micro "Roach Motels" *ACS Appl. Mater. Interfaces,* 2009 1, 48-52, incorporated by reference above. See also PCT Patent Application Serial No. PCT/US2009/063715 filed Nov. 9, 2009, which is incorporated herein by reference, for a description of hollow conjugated polyelectrolyte microcapsules (HCPEs) that are shown to have light induced antimicrobial activity.

In recent investigations we have found dark biocidal activity for a number of CPE and in at least one case we have found a CPE that shows no light-activated biocidal activity but strongly enhanced dark activity. (See e.g., Thomas S. Corbitt, Liping Ding, Eunkyung Ji, Linnea K. Ista, Katsu Ogawa, Gabriel P. Lopez, Kirk S. Schanze, David G. Whitten, "Light and Dark Biocidal Activity of Cationic Poly(arylene ethynylene) Conjugated Polyelectrolytes" *Photochemical and Photobiological Sciences,* 2009, in press, incorporated by reference, above.) We have shown that enhanced dark activity is linked with enhanced ability to associate with the bacterial membrane (step i). See, e.g., Liping Ding, Eva Y. Chi, Sireesha Chemburu, Eunkyung Ji, Kirk S. Schanze, Gabriel P. Lopez, David G. Whitten, "Insight into the Mechanism of Antimicrobial Poly(phenylene ethynylene) Polyelectrolytes: Interactions with Phosphatidylglycerol Lipid Membranes", *Langmuir,* 2009, in press, which is hereby incorporated by reference. In the process, this CPE is more likely to destroy or pass through the bacterial membrane following association.

Further studies have shown that while CPEs and OPEs are structurally diverse, they are generally amphiphillic due to the hydrophilic, charged side chains positioned along the rod-like hydrophobic PPE backbone. Dye leakage studies demonstrated a size dependent membrane perturbation against bacterial membrane mimics, with longer oligomers exhibiting higher activity than their smaller counterparts. Furthermore, the membrane perturbation activity appears to have selective with respect to specific types of membrane lipids—that is, most CPEs and OPEs perturbed bacterial but not mammalian membrane mimics Accordingly, conjugated polyelectrolytes such as CPEs and OPEs that demonstrate light or dark biocidal activity are ideal candidates for attachment to or formation of fibrous materials in order to produce textiles or other soft surfaces having antimicrobial properties.

According to various embodiments, it may be desirable to have the CPE or OPE robustly attached to the fibers, for example via covalent linkages. According to some embodiments, attachment of the CPE or OPE via chemisorption and physisorption may also be used.

In chemisorptions, a textile substrate is chemically activated with a primer or initiator and then reacted with a polymer or prepolymer to graft the conjugated polyelectrolyte to the surface in a step growth polymerization process. An exemplary chemisorption scheme employing a step growth polymerization process is shown in FIG. 2. Alternate reaction schemes may employ a living polymerization mechanism utilizing molecule by molecule propagation starting from a single molecule initiator.

In physisorption, the textile and conjugated polyeletrolyte are mixed under appropriate conditions such that the positively charged polymer attaches to the negatively charged textile surface. Typically the CPE or OPE is dissolved in a solvent (e.g., water or methanol) and the fabric is "dyed" with the solution.

Alternatively, according to still an embodiment, an initial organosilane attachment may be used as a synthetic approach to accomplish surface grafting. See, e.g., Ogawa, K.; Chemburu, S.; Lopez, G. P.; Whitten, D. G.; Schanze, K. S. "Conjugated Polyelectrolyte-Grafted Silica Microspheres" *Langmuir,* 2007, 23, 4541-4548, which is hereby incorporated by reference. By putting an organic iodine on the substrate we have grafted CPE and OPE on nano- and micro-particles and planar surfaces. This silane approach may be used to graft CPE or OPE onto fabrics. Furthermore, this approach can be easily extended to provide more robust linkages than silanes, using modified chemistries for attaching CPE and OPE to surfaces including ester, ether and amide linkages as needed.

Furthermore the antimicrobial polymers described herein may be incorporated into or onto hard or soft surfaces using the techniques described above or, alternatively, by other known casting, electrospinning, dipping, or coating techniques. However, it is noted that the photophysical properties of CPEs and OPEs are dependent on planarity which can be affected by self-assembly onto a substrate or placement in a poor solvent. Accordingly, these factors should be considered and taken into account when selecting a particular attachment or incorporation method.

As a still further embodiment, the conjugated polyelectrolytes may themselves be formed into fibers, for example via electrospinning.

While several of the examples specifically mention the use of cotton fabrics, it will be appreciated that any other suitable fabric, including natural and/or synthetic fibers may be used. According to some embodiments, the fabric used may comprise or consist of natural fibers such as cotton, silk and/or wool, or suitable blends thereof. Blended fabrics may include only natural fibers, only synthetic fibers, or both natural and synthetic fibers. In some cases, the antimicrobial polymers described herein may be incorporated into electrospun fibers for woven fabrics including, but not limited to filters. Other suitable textiles may include, but are not necessarily limited to rayon, nylon, or blends of cotton, silk, wool or other natural fabrics or fibers with synthetic fabrics or fibers of rayon or nylon.

Potential uses of fibers may include prophylaxes for potentially contaminated surfaces including mattresses and bed linens, countertop coverings, tablecloths, curtains and various swabs, bandages, sterile mats and liners for use both inside and outside a sterile/clinical environment or in food-preparation areas. Their uses may be directed against known contamination, as in a wound infection, or applied as a deterrent to propagation of pathogenic agents in such applications as coverings for common fomites. Treatments of the compounds onto various cellulosic components would also enable their use as filter elements for water purification.

Different blends to specifically release or retain killed bacteria could be developed based on combination of polymers with the desired retention properties. This could be effected either by use of varied polymer proportions in a single layer coating or by building multiple layers with the required external affinities.

According to some embodiments, the antimicrobial polymers described herein may be used as antimicrobial coatings for or otherwise incorporated into a variety of materials having commercial, industrial and/or household applications. For the purposes of this application, it should be noted that the term "material" incorporates both "soft" and "hard" substances including organic and inorganic matter such as, but not limited to, natural and man-made fabrics, plant-based materials, metals, polymers, wood, stone, plastic, and the like.

Examples of suitable medical applications for the antimicrobials described herein include bedsheets, hospital garments, curtains, floor and wall materials, air filtration systems, medical devices, bandages, surgical instruments, gloves, masks, lab coats, gauze orthopedic prostheses, bedding, bed frames, mattress covers, surgical furniture, dividers, curtains, carts for transport of medication, linens, dental trays, incise drapes, wound dressings, and implants.

Applications for the building industry include the coating or incorporation of antimicrobial polymers in wall laminates, hand rails, pulls, trims, door handles, slings, hoists, window blinds, paints, sealants, polishes, and plastics.

Other applications include antimicrobial coatings for keyboards, gaming devices, toys, (for example, but limited to, in a daycare environment), industrial, commercial and household kitchens, food preparation equipment and utensils or any other surface where a sterile environment is desirable.

According to various embodiments, the antimicrobial polymers described herein may be incorporated into various aspects of filtrations devices. For example, the antimicrobial polymers may be incorporated into filter elements for air filtration systems such as those used in commercial or residential buildings, cars, buses, trains airplane cabins etc. Alternatively or additionally, the antimicrobial polymers may be incorporated into commercial or household water or other liquid filtration systems by application of coatings on equipment and incorporation into and/or coating on filters. Alternatively or additionally, the antimicrobial polymers described herein may be utilized in recoverable bacterial absorbents (by filtration or magnetic components) in the form of coated beads or other suitable substrates. Furthermore, they may be incorporated in separation membranes for bacterial exclusion, extraction, and/or immobilization. They may also be incorporated into or used as a coating for disposal bags for biological waste or other (potentially) contaminated materials.

Specific polymer combinations and directed multilayer constructs may lend themselves to either single use or multiple uses, depending on the sequestration properties of that given combination. The coatings that have a high affinity for microbial binding would lend themselves more to single use applications (i.e. bandages or wipes) and those that would release microbial material, either upon washing or other decontamination could undergo multiple uses (i.e. bed linens, tablecloths).

As indicated above, we have grafted CPE to cotton and mixed cotton-nylon fabrics and we find that the CPE grown covalently from the fabric show uniform color and fluorescence. We have also found that these fabrics show the ability to capture and kill, in a light activated process, pathogenic Gram negative *Pseudomonas aeruginosa* strain PAO1.

We performed confocal laser scanning microscopy to obtain images of *Bacillus atrophaeus* bacteria attached to fabric in dark conditions. The images showed that the entrapped bacteria were mostly dead (with a few live bacteria) and that they were clearly identifiable as bacteria.

Confocal microscopic images of mixed cotton-nylon fabric after DABCO polymer-grafting, exposure to *P. aeruginosa*, and then light exposure for 30 minutes showed that attachment and killing of the bacteria was seen on the polymer-coated samples, but not on untreated gauze control samples.

In a subsequent study we have tested the same fabric in the dark and the light against Gram positive *Bacillus atrophaeus*. In the first test with this bacterium we found that untreated fabric was ineffective at attaching and killing the bacteria in dark or in visible light irradiated samples. In contrast, agitation of a suspension of *Bacillus atrophaeus* with fibers of a CPE-derivatized cloth resulted in attachment and killing of the bacteria. Interestingly, in the light samples the bacteria were observed to have thickly coated the polyelectrolyte grafted fibers and the bacteria appeared to be degraded to a plaque which likely cannot be removed from the fabric by simple rinsing or agitation.

The dark killed bacteria are less abundant and easily recognized as killed but not degraded *B. atrophaeus*. These results suggest that the binding of the conjugated polyelectrolytes on what is a "soft surface" may lead to enhanced biocidal activity compared to the polymer grown from "hard" planar or microsphere surfaces from silica. It has also been found that a sample of all-cotton gauze can be derivatized with the CPE by a similar procedure and that this material exhibits a strong and uniform fluorescence when activated by visible light that corresponds to excitation of the CPE. Treatment of these samples with *B. atrophaeus* in the dark and under irradiation with visible light results in similar killing.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications. The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The one or more inventions illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

EXPERIMENTS

Materials and Methods

Bacterial Strain.

*Bacillus atrophaeus* (ATCC) was obtained as a lyophilate from the American Type Culture Collections (Baltimore, Md.), revived in Tryptic Soy Broth (TSB; Difco) and stored in TSB with 20% (w/w) glycerol (EMD) at −70° C. until use. Stock cultures maintained on agar (2%, Difco) slants of TSB were used to inoculate 50 mL cultures in liquid TSB. Cultures were grown at 30° C. for 18 hr. Cells were collected by centrifugation at 4.4 kRPM (g=X) in a XXXX centrifuge for 20 min Cells were resuspended in 50 mL 0.85% (w/v) NaCl (source) and recentrifuged. This wash was repeated 1×. The final pellet was suspended in 50 mL 0.85% NaCl and adjusted to 107 cells/mL for biocide testing.

Surface Grafting.

DABCO was grafted onto untreated cotton fibers according to the reaction scheme in FIG. 1. Three to four pieces of fiber samples (~100 mg) were refluxed for 6 hours in 10 mL of toluene along with (100 mg, 0.24 mmol) 4-Iodo-N-[3-(trimethoxysilyl)propyl]benzamide (1), synthesized according to the method described previously. (See e.g., Ogawa, K., S. Chemburu, G. P. Lopez, D. G. Whitten, and K. S. Schanze. 2007. Conjugated polyelectrolyte-grafted silica microspheres. *Langmuir* 23:4541-4548). The surface modified fiber samples were collected and washed with acetone several times. The fabric pieces were dried under vacuum overnight.

Surface-modified fiber samples (Fiber-Ad, 4 pieces, ~100 mg), were suspend in 15 mL DMF and 3 mL isopropylamine with compound 2 (56.6 mg, 0.051 mmol), compound 3 (6.4 mg, 0.051 mmol), CuI (1 mg, 5.6 µmol), and $PdCl_2(PPh_3)_4$ (2 mg, 2.8 µmol). The resulting suspension was purged with argon for 30 min and stirred at 60° C. for 12 h. The polymer-grafted fiber pieces were air dried and washed several time with methanol, THF, a dilute solution of SDS and water. Washes were repeated until the supernatant solution exhibited no yellow color with blue fluorescence under a UV lamp. Finally, the fiber pieces were rinsed with methanol and were dried under vacuum overnight.

Alternate Attachment Method—Physisorption.

Fiber samples were soaked in $10^{-4}$ M aqueous solution of conjugated polyelectrolyte (CPE) and stirred gently for different time intervals (ranging from 1 h-12 h). The soaked fiber pieces were air dried and washed several times with methanol, THF, dilute solution of sodium dodecyl sulfate (SDS) and water. Washes were repeated until the supernatant solution exhibited no yellow color with blue fluorescence under a UV lamp. Finally, the fiber pieces were rinsed with methanol and dried under vacuum overnight.

Biocidal Testing.

2 mg of DABCO grafted cotton (DGC) or untreated cotton (UC) were placed into 1 mL microcentrifuge tubes (VWR). Dark control samples were placed into black centrifuge tubes. 1 mL of bacterial suspension ($10^7$ cells/mL in 0.85% NaCl) were added to the fiber samples. The samples were then incubated at reactor temperature for 30, 60 or 120 min in a LuzChem ORG photoreactor using Sylvania T5 ($\lambda$=350-799 nm) lamps. After incubation time 3 µL Syto 24 (Invitrogen) and 3 µL propidium iodide (Invitrogen) were added to the tubes and incubated in the dark for 15 minutes.

The samples were removed and examined by confocal laser scanning microscopy (see below) and the supernatants by flow cytometry. For analysis of cell uptake, 10 µL of sample was removed for counting in a hemocytometer (brand).

SEM.

For SEM studies, dry cotton samples were mounted on carbon adhesive tabs on aluminum specimen mounts. Samples were rendered conductive with Au/Pd, (Denton Desk II sputter coater). Samples were examined with a Hitachi S-4000 field-emission scanning electron microscope and digital micrographs were acquired with PCI Quartz software.

Fluorescence and Absorbance.

Steady state fluorescence emission spectra were recorded on a Jobin-Yvon Fluorolog-3 fluorimeter in front-face mode for the fiber samples. UV-vis absorption spectra were obtained on a Perkin-Elmer Lambda 25 dual-beam absorption spectrometer.

Flow Cytometry.

Data were gathered using a Accuri model C6 flow cytometer. The format used for analysis of the sample sets is side scatter (height) vs. red fluorescence (670 nm long pass) (height). The red (dead) intensity shows some minor fluctuations between sample sets, which we believe to be due to fabric absorption of the stain. However, the populations are still clearly separated in most cases and can be quantified accordingly. The use of side scatter also eliminates the other simultaneous and differential stain absorption shift (of the SYTO stain) that is observed when plotting green vs. red fluorescence. Event thresholds were set on forward scatter, 20,000-80,000, according to bacterial sizes, and a secondary threshold of ~250 was used on a fluorescence channel (usually FL3, 670 1p).

Confocal Laser Scanning Microscopy.

Fiber samples were examined on a LSM 510-Meta (Zeiss, Jena, Germany) confocal laser scanning microscope. A 488 nm line from a 30 mW Ar laser was used to excite the cell permeant (live) Syto 25. The 543 nm line from a 1 mW HeNe laser was used to excite cell impermeant (dead) stain propidium iodide. Imaging was done using a 63× long working distance objective (NA).

Results

FIGS. 3 and 4 show scanning electron micrographs of individual untreated (FIG. 3) and SGD (FIG. 4.) cotton fibers. These images demonstrate the accumulation of DABCO on the cotton. That this is indeed DABCO is suggested by FIG. 5, which shows the absorbance and fluorescence peaks of SGD-ABCO cotton and a representative scan of the unbound polymer.

Figure 5:
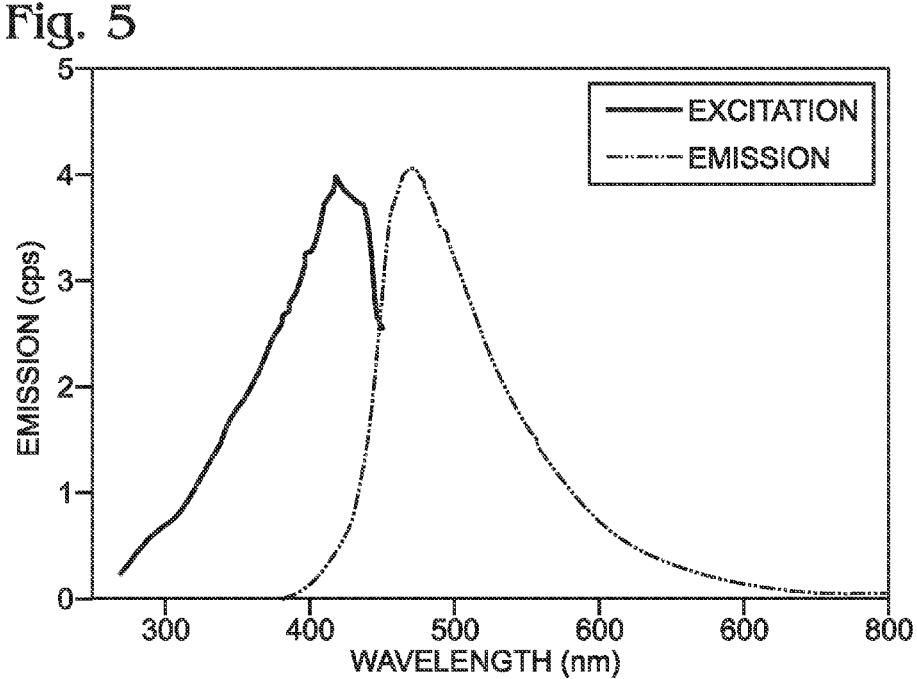
FIG. 5 shows the absorbance and fluorescence peaks of SGDABCO cotton and a representative scan of the unbound polymer.

Confocal laser scanning images (FIGS. 6-9) show the uptake and killing of *B. atrophaeus* vegetative cells on DABCO-cotton fibers. When compared to untreated cotton, DABCO-cotton can be seen to take up a large number of cells in both the light and the dark. Many of these cells are contained within the spaces between the fibers and are still motile. Cells attached to fibers treated with light are killed and lose shape, forming "plaques" on the surface of the fibers. FIG. 9 shows that by 120 min, almost all bacteria are collocated on the fibers. FIG. 5 shows a multilayer of cells on the end of the fiber.

The uptake of cells was also measured using flow cytometry. FIG. 10 demonstrates the number of cells present in the suspending fluid over time. After two hours, the number of cells has decreased to 6% of the original suspension. The suspended cells were also monitored for their survival. FIG. 11 shows the proportion of live and dead cells suspended with treated and untreated cotton fiber. The dark killed ~94% of 63966 cells counted while the light killed ~88% of the suspended cells. The reduced killing in the light may be due to inactivation of the polymer by long exposure to light.

Discussion

We have demonstrated successful grafting of DABCO to cotton fiber, with both SEM evidence of polymer accumulation and fluorescence evidence that the photoproperties of SGD match that of the dissolved polymer. Although this method is good for a cellulosic based fiber, such as cotton, we found in a mixed cotton-nylon blend, that the DABCO bound only to the cotton fibers (data not shown).

DGC takes up a substantial number of bacteria. According to flow cytometric data, 94% of the bacteria were retained by the DGC after removal from the bacterial suspension. CSLM pictures show that even living cells seem to be corralled within the spaces between the DGC, but not untreated cotton, fibers. We have observed such clustering on both DABCO-treated beads (Chemburu, S., T. S. Corbitt, L. K. Ista, E. Ji, J. Fulghum, G. P. Lopez, K. Ogawa, K. S. Schanze, and D. G. Whitten. 2008. Light-induced biocidal action of conjugated polyelectrolytes supported on colloids. Langmuir 24:11053-11062.) and in micro roach motels (Corbitt, T. S., J. R. Sommer, S. Chemburu, K. Ogawa, L. K. Ista, G. P. Lopez, D. G. Whitten, and K. S. Schanze. 2009. Conjugated Polyelectrolyte Capsules: Light-Activated Antimicrobial Micro "Roach Motels". Acs Applied Materials & Interfaces 1:48-52). The ability of DGC to remove so many bacteria from a wet environment points to their efficacy against pathogens released by sneezing or coughing, or spills.

DGC killed ~95% of the bacteria left in suspension. The number that were killed while in contact with the fibers is harder to assess. We did observe the formation of "plaques" of propidium iodide staining material on the fibers exposed to light, especially after two hours, which suggests that cells are destroyed during the process and we were seeing smears of nucleic acid on the surface. It appears that in some cases, some multilayers of cells were formed (TOC image) presumably over cellular debris.

We also tested DGC against spores of *B. atrophaeus*. Although ~50% of the spores were killed in suspension (as measured by flow cytometry, data not shown), the spores were not significantly entrapped by the fibers, decreasing their chance of contact with the spores. The surface properties of *Bacillus* sp. spores have recently been analyzed and found to be quite hydrophilic (water contact angle of)20-30° (Chen, G., A. Driks, K. Tawfiq, M. Mallozzi, and S. Patil. 2010. *Bacillus anthracis* and *Bacillus subtilis* spore surface properties and transport. Colloids and Surfaces B-Biointerfaces 76:512-518), whereas bacterial adhesion to hydrocarbon studies suggest that *Bacillus sp* vegetative cells range from being slightly to very hydrophobic. (Thwaite, J. E., T. R. Laws, T. P. Atkins, and H. S. Atkins. 2009. Differential cell surface properties of vegetative *Bacillus*. Letters in Applied Microbiology 48:373-378). In preliminary studies on DABCO grafted nylon/cotton fabric, however, *Pseudomonas aeruginosa*, PAO1, which under our growth conditions also prefers hydrophilic surfaces for attachment, is just as effectively retained and killed as is *B. atrophaeus* (data not shown).

What is claimed is:

1. A composition of matter comprising a fibrous material having poly(phenylene ethynylene)-based cationic conjugated polyelectrolyes bonded thereto, the composition being prepared by contacting a fibrous material comprising a fiber-forming polymer having iodophenyl groups bonded thereto and a di-iodo reagent of formula (2)

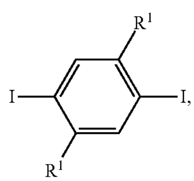

wherein $R^1$ is a DABCO group of formula 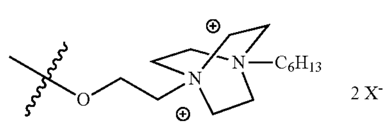 wherein X is an anion and a wavy line indicates a point of bonding and a phenyl-diyne reagent of formula (3)

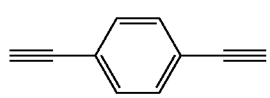

in the presence of a catalyst comprising palladium(0) and CuI under conditions suitable to provide the fiber-forming polymer having the poly(phenylene ethynylene)-based cationic conjugated polyelectrolyte covalently bonded thereto, the fibrous material comprising the fiber-forming polymer exhibiting biocidal activity.

2. The composition of matter of claim 1, wherein the fiber-forming polymer having iodophenyl groups bonded thereto is prepared by treating a fiber-forming polymer having hydroxyl groups with a compound having a hydroxyl-reactive group and an iodophenyl group, under conditions suitable to bring about reaction of the hydroxyl group and the hydroxyl-reactive group, wherein the compound having a hydroxyl-reactive group and an iodophenyl group is of formula

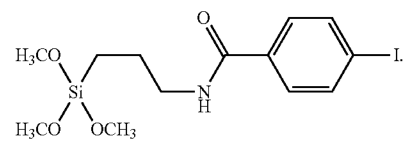

3. The composition of matter of claim 1 wherein the fiber-forming polymer having iodophenyl group bonded thereto is prepared from a polymer selected from the group consisting of cotton, silk, wool, rayon, and blends thereof.

4. The composition of matter of claim 1 wherein the fibrous material is selected from the group consisting of cotton, silk, wool, rayon, nylon, and blends thereof.

5. The composition of matter of claim 1 wherein the composition exhibits light-activated biocidal activity.

6. The composition of matter of claim 1 wherein the composition exhibits dark biocidal activity.

7. The composition of matter of claim 1 wherein the conjugated polymers generate singlet $O_2$.

8. The composition of matter of claim 1 wherein the conjugated polymers perturb prokaryotic cell membranes.

9. A fabric comprising the composition of matter of claim 1.

10. An article of clothing comprising the composition of matter of claim 1.

11. Linens comprising the composition of matter of claim 1.

12. A surgical instrument comprising the composition of matter of claim 1.

13. A filtration system comprising the composition of matter of claim 1.

14. A bandage comprising the composition of matter of claim 1.

15. A floor or wall material comprising the composition of matter of claim 1.

16. A method of forming an antimicrobial composition of matter comprising contacting a fibrous material comprising a fiber-forming polymer having iodophenyl groups bonded thereto and a di-iodo reagent of formula (2)

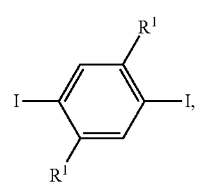

wherein $R^1$ is a cationic group, and a phenyl-diyne reagent of formula (3)

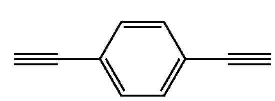

in the presence of a catalyst comprising palladium(0) and CuI under conditions suitable to provide the fiber-forming polymer having the poly(phenylene ethynylene)-based cationic conjugated polyelectrolyte covalently bonded thereto, the fibrous material comprising the fiber-forming polymer.

17. The method of claim 16, wherein the antimicrobial composition exhibits light-activated antimicrobial bioactivity.

* * * * *

UNITED STATES PATENT AND TRADEMARK OFFICE
CERTIFICATE OF CORRECTION

| | | |
|---|---|---|
| PATENT NO. | : 8,598,053 B2 | Page 1 of 1 |
| APPLICATION NO. | : 13/503067 | |
| DATED | : December 3, 2013 | |
| INVENTOR(S) | : Whitten et al. | |

It is certified that error appears in the above-identified patent and that said Letters Patent is hereby corrected as shown below:

In the Claims:

In column 11, line 27, in Claim 1, delete "polyelectrolyes" and insert --polyelectrolytes--, therefor Signed and Sealed this
Sixth Day of May, 2014

Michelle K. Lee
*Deputy Director of the United States Patent and Trademark Office*